United States Patent
Bak et al.

(10) Patent No.: US 10,973,190 B2
(45) Date of Patent: Apr. 13, 2021

(54) *VRIESEA* 'HAPPYYELLOW'

(71) Applicant: Corn Bak BV, Assendelft (NL)

(72) Inventors: Elly Bak, Rijsenhout (NL); Nicolaas Steur, Oude Niedorp (NL)

(73) Assignee: Corn Bak B.V.

( * ) Notice: Subject to any disclaimer, the term of this patent is extended or adjusted under 35 U.S.C. 154(b) by 0 days.

(21) Appl. No.: 16/573,327

(22) Filed: Sep. 17, 2019

(65) Prior Publication Data

US 2021/0076595 A1    Mar. 18, 2021

(51) Int. Cl.
*A01H 6/22* (2018.01)
*A01H 5/10* (2018.01)

(52) U.S. Cl.
CPC .............. *A01H 6/228* (2018.05); *A01H 5/10* (2013.01)

(58) Field of Classification Search
CPC ...................................... A01H 6/228
USPC ......................................... Plt./370
See application file for complete search history.

(56) References Cited

U.S. PATENT DOCUMENTS

PP19,071 P2 *   8/2008   Bak .......................... A01H 5/02
Plt./370

* cited by examiner

*Primary Examiner* — David H Kruse
(74) *Attorney, Agent, or Firm* — Cassandra Bright

(57) ABSTRACT

A new and distinct *Vriesea* plant named 'HAPPYYELLOW' characterized as a funnel-form rosette plant, measuring about 25 cm in height (above the pot when flowering) and 35 cm in diameter; bipinnate spike inflorescence, measuring about 40 cm in height and about 25 cm in diameter, and yellow (closest to RHS 7A) in color; and linear-lanceolate foliage, measuring about 25 cm in length and about 2.5 cm to 3.5 cm in width, and green (RHS 137A) in color.

5 Claims, 2 Drawing Sheets
(2 of 2 Drawing Sheet(s) Filed in Color)

VRIESEA 'HAPPYYELLOW'

FIELD OF THE INVENTION

The present invention relates to a new, distinct and stable hybrid of *Vriesea* plant, hereinafter referred to as 'HAPPYYELLOW'. The present invention relates to seeds which are the *Vriesea* hybrid 'HAPPYYELLOW', as well as, plants and plant parts produced by these seeds which have all of the morphological and physiological characteristics of the *Vriesea* hybrid 'HAPPYYELLOW'. The present invention also relates to methods for producing these seeds and plants of the *Vriesea* hybrid 'HAPPYYELLOW'. Furthermore, the present invention relates to a method of producing progeny *Vriesea* plants by crossing *Vriesea* 'HAPPYYELLOW', as either the female or seed or male or pollen parent, with another *Vriesea* plant and selecting progeny.

BACKGROUND OF THE INVENTION

The present invention relates to a new, distinct and stable hybrid of *Vriesea* hybrid, and hereinafter referred to by the variety denomination 'HAPPYYELLOW'. The new *Vriesea* 'HAPPYYELLOW' originated from a cross made in a controlled breeding program by the inventors in 2010, and then first flowered in 2015, in Assendelft, The Netherlands. The female or seed parent is the unnamed *Vriesea* selection identified by code 870612 (unpatented). The male or pollen parent is the unnamed *Vriesea* selection identified by code 1003092 (unpatented).

*Vriesea* is a member of the Bromeliaceae family. *Vriesea* is predominantly epiphytic and the genus of about 250 species are found in forested and rocky areas in Mexico, Central America, West Indies and South America. For the most part, species have rosettes of glossy, sword-shaped, smooth-edged leaves.

Floral bracts of *Vriesea* frequently have brilliant colors and may last for many months. The range of colors for *Vriesea* is generally from yellow through orange but may also include flame red and deep red-purple. White, yellow, or green tubular, three-petalled flowers may also appear on a stem or within the leaf rosette but are usually short-lived.

*Vriesea* may be advantageously grown as pot plants for greenhouse or home use. Typically, the plants are shaded from direct sunlight. During the spring to autumn period, the central vase-like part of the leaf rosette is normally filled with water.

*Vriesea* is native to tropical America. Leaves of *Vriesea* are usually formed as basal rosettes which are stiff and entire and in several vertical ranks. *Vriesea* plants have terminal spikes or panicles which are often bracted with petals united in a tube about as long as the calyx. The ovary is superior and the seeds plumose.

Asexual propagation of *Vriesea* is frequently performed by vegetative means through the use of tissue culture practices. Propagation of *Vriesea* can also be from offshoots which can be detached from the mother plant and grown in an appropriate soil or bark mixture.

Methods for cultivation and crossing of *Vriesea* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Vriesea* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Vriesea* cultivars with attractive ornamental features. Additionally, a need exists for additional *Vriesea* hybrid cultivars that can be easily propagated by seed. The new *Vriesea* 'HAPPYYELLOW' was developed through a controlled breeding program and exhibits unique, desirable and stable characteristics.

SUMMARY OF THE INVENTION

The present invention provides *Vriesea* plant selections that are solid long-lasting hybrids with red-yellow inflorescence that exhibit good keeping quality. The present invention also provides *Vriesea* plant selections with a bipinate spike inflorescence with a unique yellow color which distinguishes the new cultivar from typical *Vriesea*.

These and other objectives have been achieved in accordance with the present invention which provides 'HAPPYYELLOW' as a new *Vriesea* cultivar that is a product of a planned breeding program conducted by the inventors, Elly Bak and Nico D. M. Steur, in Assendelft, The Netherlands, in 2010. The female or seed parent is the unnamed *Vriesea* selection identified by code 870612 (unpatented). The male or pollen parent is the unnamed *Vriesea* selection identified by code 1003092 (unpatented).

Both parental cultivars have a sufficient degree of homozygosity such that the progeny of the cross are genotypically and phenotypically uniform. The new hybrid 'HAPPYYELLOW' therefore can be produced by sexual reproduction by crossing the parental inbred lines identified by the codes 870612 and 1003092 to produce a population of progeny plants, each of which has the combination of characteristics as herein disclosed for the new hybrid 'HAPPYYELLOW'.

Seeds which are the hybrid 'HAPPYYELLOW' are produced by crossing the parental inbred lines identified by the codes 870612 and 1003092, and are deposited with the NCIMB, Ferguson Building, Craibstone Estate, Bucksburn, Aberdeen, AB21 9YA, United Kingdom. NCIMB Patent Deposit Designation No. NCIMB-43443. 2500 seeds were deposited with the NCIMB on Jul. 22, 2019.

OBJECTS OF THE INVENTION

The present invention relates to seeds which produce *Vriesea* hybrid 'HAPPYYELLOW'. The present invention also relates to *Vriesea* plants, and parts thereof, having all the physiological and morphological characteristics of *Vriesea* hybrid 'HAPPYYELLOW'. The present invention relates to a plant produced from seeds which are *Vriesea* hybrid 'HAPPYYELLOW'. The present invention also relates to plant parts, such as pollen, seeds or inflorescence produced by *Vriesea* hybrid 'HAPPYYELLOW'.

The present invention relates to a method of producing seed which are *Vriesea* hybrid 'HAPPYYELLOW', by (a) crossing the unnamed *Vriesea* selection identified by code 870612 (unpatented) as the female or seed parent with the unnamed *Vriesea* seletion identified by code 1003092 (unpatented) as the male or pollen parent, and the reciprocate cross with 100309 as the female parent and 870612 as the male parent, and (b) harvesting seeds produced from said crosses.

The present invention also relates to a method of producing plants having all the physiological and morphological characteristics of the *Vriesea* hybrid 'HAPPYYELLOW' comprising the steps of (a) crossing the unnamed *Vriesea* selection identified by code 870612 (unpatented) as the female or seed parent with the unnamed *Vriesea* selection identified by code 100309 (unpatented) as the male or pollen parent, and the reciprocate cross with 100309 as the female parent and 870612 as the male parent; (b) harvesting seeds produced from said cross; and (c) producing plants from said harvested seeds.

The present invention also relates to producing progeny plants from the cross of *Vriesea* hybrid 'HAPPYYELLOW', as the female or male parent, with another *Vriesea* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Vriesea* hybrid 'HAPPYYELLOW' showing the colors as true as is reasonably possible with colored reproductions of this type. Colors in the photographs may differ slightly from the color values cited in the detailed botanical description which accurately describes the color of 'HAPPYYELLOW'.

Figure 1:
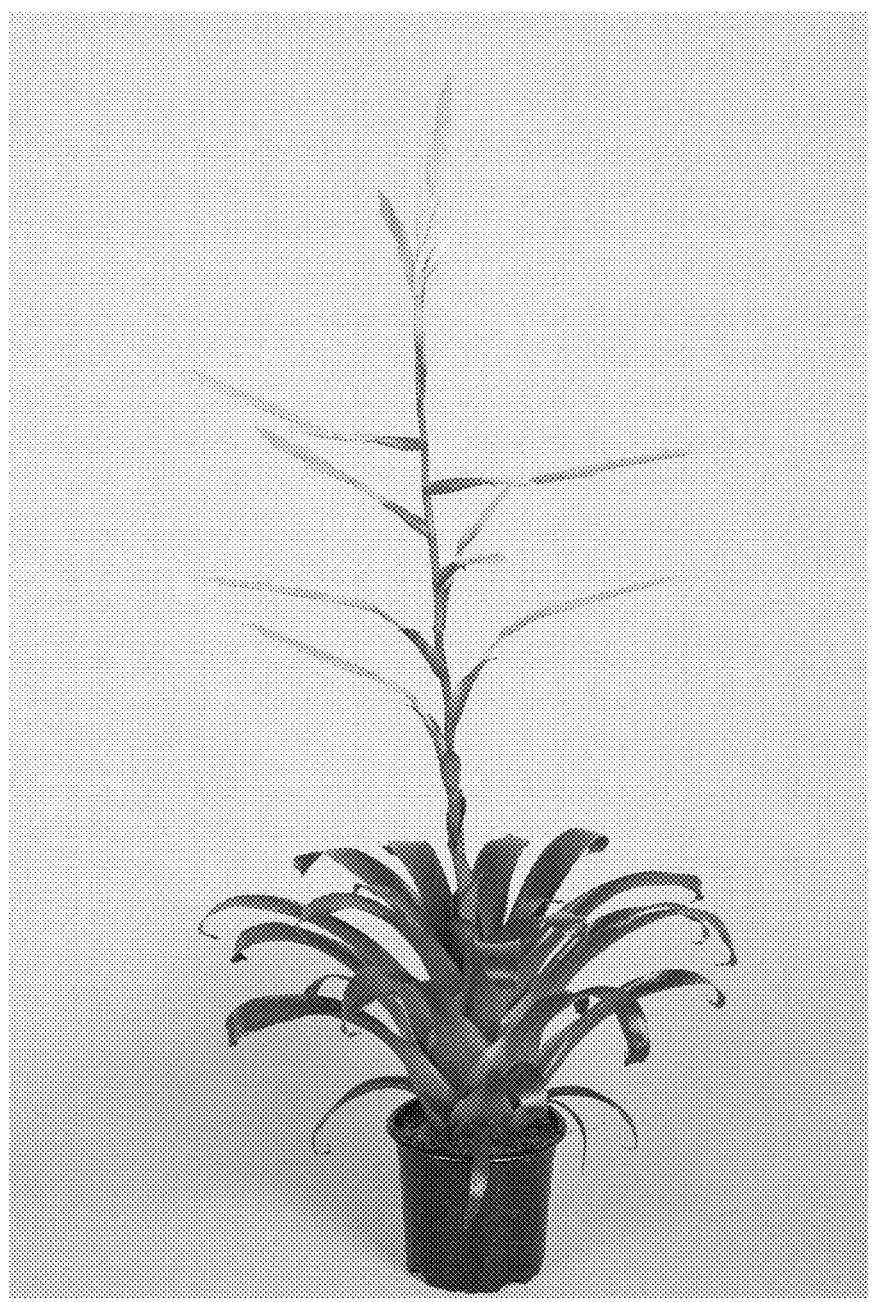
FIG. 1 shows a side view perspective of a typical potted, flowering plant of 'HAPPYYELLOW', at 11 months of age from potting size.
Figure 2:
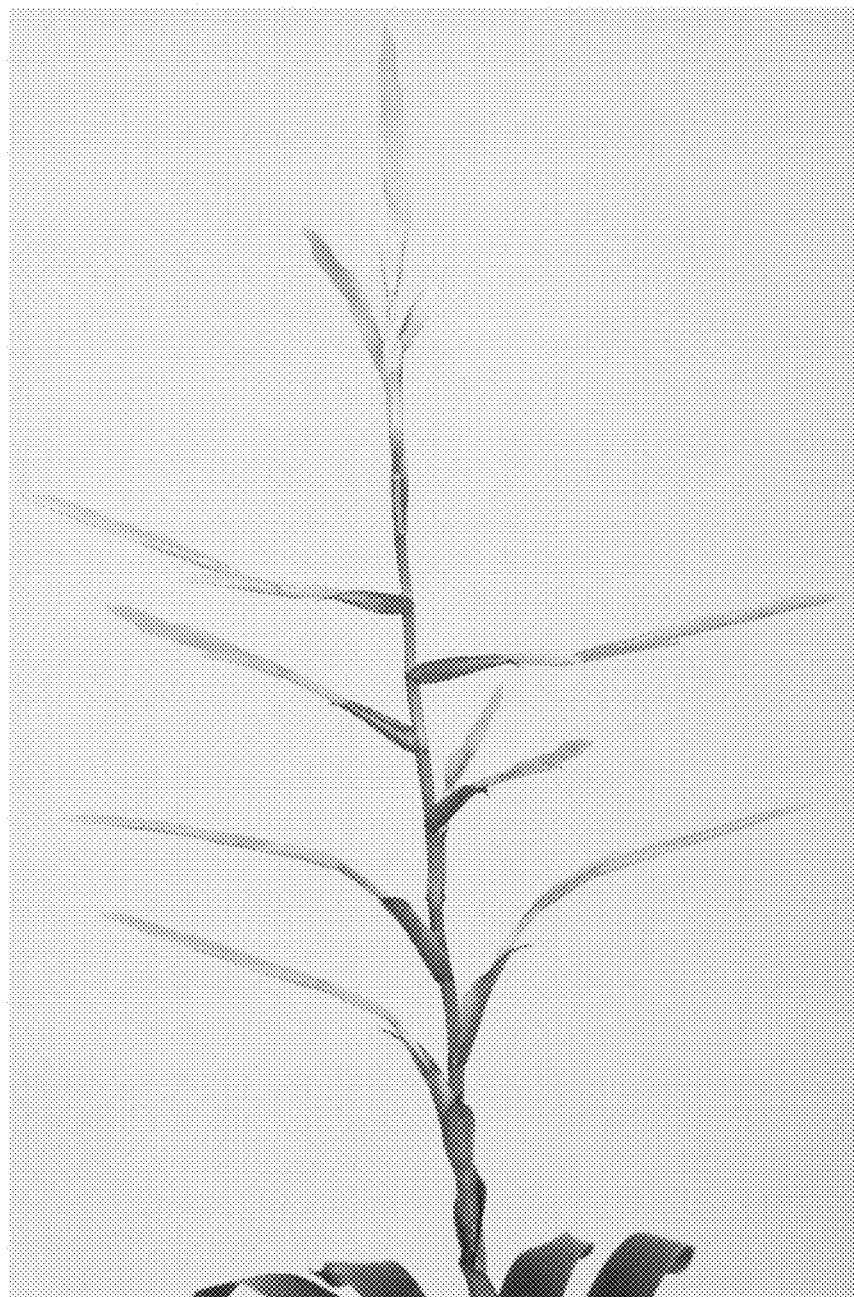
FIG. 2 shows a close-up side view perspective of the inflorescence and top bracts produced by a typical potted, flowering plant of 'HAPPYYELLOW', at 11 months of age from potting size.

The present invention was created by the inventors, Elly Bak and Nicolaas D. M. Steur in 2010, and flowered for the first time in 2015 in Assendelft, The Netherlands.

This invention is directed to *Vriesea* plant having all the morphological and physiological characteristics of the hybrid 'HAPPYYELLOW' produced from seeds which are the product of the cross of the unnamed *Vriesea* selection identified by code 870612 (unpatented) as the female or seed parent with the unnamed *Vriesea* selection identified by code 1003092 (unpatented) as the male or pollen parent. Both parents have a sufficient degree of homozygosity such that the progeny of the cross were, and continue to be, phenotypically uniform. The new hybrid 'HAPPYYELLOW' can therefore be produced by sexual reproduction by crossing of the inbred selections identified by the codes 870612 and 1003092 to produce a population of progeny plants, each of which has the combination of characteristics herein disclosed for the new hybrid 'HAPPYYELLOW'.

The new hybrid 'HAPPYYELLOW' can also be produced by asexually reproducing progeny from the cross of the parental inbred lines identified by the codes 870612 and 1003092. Asexual reproduction of the new cultivar by vegetative means by cuttings was first performed in 2015, in Assendelft, The Netherlands. The first 'HAPPYYELLOW' plants propagated through the use of such cuttings flowered in 2016, in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'HAPPYYELLOW' which in combination distinguish this *Vriesea* as a new and distinct cultivar:
1. Funnel-form rosette plant, measuring about 60 cm in height (above the pot when flowering) and 35 cm in diameter;
2. Panicle inflorescence, measuring about 40 cm in height and about 16 cm in diameter, and yellow (closest to RHS 7A) in color;
3. Linear-lanceolate foliage, measuring about 25 cm in length and about 2.5 cm to 3.5 cm in width, and green (RHS 137A) in color.

Of the many commercial plants known to the present inventors, the most similar in comparison to the new *Vriesea* hybrid 'HAPPYYELLOW' is the *Vriesea* species delicatula (unpatented). Plants of the new hybrid 'HAPPYYELLOW' differ from plants of *V. delicatula* primarily in size, with the new variety producing a larger plant. Furthermore, plants of 'HAPPYYELLOW' produce inflorescences which have yellow floral bracts, whereas plants of *Vriesea* delicatula produce inflorescences with yellow-green bracts.

'HAPPYYELLOW' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced. Since treatment to induce flowering disrupts normal watering and fertilization regimens, flowering treatment of relatively smaller plants adversely affects the growth of the plant.

The aforementioned photographs, together with the following observations, measurements and values describe the new *Vriesea* 'HAPPYYELLOW' as grown in a greenhouse in Assendelft, The Netherlands, under conditions which closely approximate those generally used in commercial practice. Plants of 'HAPPYYELLOW' were grown in a greenhouse with day temperatures ranging from 20° C. to 28° C. and night temperatures ranging from 18° C. to 23° C. No artificial lighting or photoperiodic treatments were conducted, but plants of 'HAPPYYELLOW' are forced into flowering. The following fertilizer is added when growing plants of 'HAPPYYELLOW': 1 part nitrogen, 0.6 parts phosphor, 2 parts Kalium and 0.1 parts magnesium.

DETAILED BOTANICAL DESCRIPTION

Color references are made to the Royal Horticultural Society Colour Chart (RHS), 2001 Edition, except where general colors of ordinary significance are used. Color values were taken under daylight conditions in a greenhouse in Assendelft, The Netherlands. The age of the plants of 'HAPPYYELLOW' described is about 11 months from potting size.
Classification:
Botanical: *Vriesea* sp.
Parentage:

Female or Seed Parent: *Vriesea* selection designated 870612 (unpatented)
Male or Pollen Parent: *Vriesea* selection designated 1003092 (unpatented)
Plant:
General Appearance and Form:
  Height: About 60 cm (when flowering)
  Width: About 35 cm
  Shape: Funnel form rosette
Growth habit: Stemless
Plant Vigor: Good
Flowering Season: A fully grown plant can flower year round, starting 11 weeks after induction of natural light or through flowering treatment.
Duration of Bloom: Each flower blooms one (1) day and the total blooming of the whole inflorescence is about five (5) weeks.
Cold Tolerance: Frost tender. Temperatures below 5° C. may damage plants.
Fragrance: None
Foliage:
Quantity: About 25 (depending on size of the plant)
Size of Mature Leaf:
  Length: About 25 cm
  Width: About 2.5 cm to 3.5 cm
Overall Shape: Linear, lanceolate
Apex Shape: acuminate
Base Shape: Strap-like around central axis
Margin: Entire
Texture: Smooth
Orientation: Leaf blades arch continuously from base.
  Color: Leaf color can vary somewhat depending on growing conditions
    Mature and Immature:
      Upper surfaces: Green, RHS 137A
      Under surfaces: Green, RHS 137B
Venation: None
  Pattern: None
Inflorescence:
Quantity and Form: 1 flower per floral bract, typical for the genus *Vriesea*; flowering is normally in progression from base to tip of scape.
Borne: Erect
Shape: Bipinnate spike (main spike about 20 cm in length and about 6 cm in width, side spike about 16 cm in length and about 3 cm in width)
Size:
  Height: About 40 cm
  Diameter: About 2 cm to 3 cm
Color: Yellow, RHS 7A, space color Red, closest tom RHS 53B
Corolla:
  Form: Long and narrow, petals and sepals fused at the base around the ovary
  Number: About 45 depending on the size of plant
Petals:
  Number: 3 per flower
  Length: About 4 cm
  Width: About 0.6 cm
  Overall Shape: Ligulate
  Apex Shape: Ovate
  Base Shape: Fused
  Color:
    Upper surface: Yellow, RHS 8A
    Under surface: Yellow, RHS 8A
Sepals:
  Number: 3 per flower
  Length: About 3 cm
  Width: About 0.8 cm
  Overall Shape: Ligulate
  Apex Shape: Acute
  Base Shape: Fused
  Color: Yellow, closest to RHS 8D
Branches:
  Quantity: about 9 (depending on the size of the plant)
  Length: About 16 cm
  Width: About 3 cm
  Color: Yellow, closest to RHS 7A
Bracts:
  Quantity of bracts on the main spike: About 8
  Arrangement: Alternate
  Size:
    Length: About 4.0 cm
    Width: About 0.8 cm
  Overall shape: Ovate, folded around the petals
  Primary bract color: Red with green tip,
  Scape bract color: Red, RHS 53B
  Reproductive Organs:
Androecium:
  Stamen:
    Number: 6 per flower
    Length: About 3.5 cm
    Diameter: About 0.1 cm
    Color: Yellow, closest RHS 4D
  Anther:
    Length: About 0.5 cm
    Color: Green, (too small to distinguish RHS value)
  Pollen:
    Amount: too small to count
    Color: Yellow, (too small to distinguish RHS value)
Gynoecium:
  Pistil:
    Number: 1 per flower
    Length: About 5.3 cm
  Stigma:
    Shape: 3-parted
    Width: About 0.2 cm
    Color: Green, RHS 145C
  Style:
    Length: About 4.4 cm
    Color: Yellow, RHS 8D
  Ovary:
    Shape: Conical
    Length: About 0.5 cm
    Diameter: About 0.2 cm
    Color: Yellow-Green, RHS 150D
SEEDS/FRUIT: Not Observed
DISEASE/PEST RESISTANCE AND SUSCEPTIBILITY: Neither resistance nor susceptibility to normal diseases and pets of *Vriesea* have been observed.

We claim:

1. A *Vriesea* plant named 'HAPPYYELLOW' representative seed having been deposited at the NCIMB in Aberdeen, Scotland having accession number NCIMB 43443.

2. A *Vriesea* seed that produces the plant of claim 1.

3. A plant part obtained from the *Vriesea* plant of claim 1.

4. A method of producing a *Vriesea* progeny plant comprising the steps of (a) crossing *Vriesea* 'HAPPYYELLOW', representative seed having been deposited at the NCIMB in Aberdeen, Scotland having accession number NCIMB 43443, as a female or male parent with another *Vriesea* plant, and (b) selecting progeny.

5. The method according to claim 4, wherein the second *Vriesea* plant is 'HAPPYYELLOW'.

\* \* \* \* \*